(12) United States Patent
Zhang

(10) Patent No.: US 11,596,536 B2
(45) Date of Patent: Mar. 7, 2023

(54) DELIVERY DEVICE

(71) Applicant: LIFETECH SCIENTIFIC (SHENZHEN) CO., LTD, Guangdong (CN)

(72) Inventor: Junqiang Zhang, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 397 days.

(21) Appl. No.: 16/762,246

(22) PCT Filed: Nov. 2, 2018

(86) PCT No.: PCT/CN2018/113566
§ 371 (c)(1),
(2) Date: May 7, 2020

(87) PCT Pub. No.: WO2019/091329
PCT Pub. Date: May 16, 2019

(65) Prior Publication Data
US 2020/0345525 A1    Nov. 5, 2020

(30) Foreign Application Priority Data

Nov. 9, 2017   (CN) .......................... 201711097891.7
Jul. 26, 2018  (CN) .......................... 201810837954.6

(51) Int. Cl.
*A61F 2/95* (2013.01)
(52) U.S. Cl.
CPC ...................................... *A61F 2/95* (2013.01)
(58) Field of Classification Search
CPC .......... A61F 2/95; A61F 2/9517; A61F 2/954; A61F 2/962; A61F 2/966; A61F 2/9661;
(Continued)

(56) References Cited

U.S. PATENT DOCUMENTS

| 2005/0027305 | A1  | 2/2005 | Shiu et al. |
| 2009/0105798 | A1* | 4/2009 | Koch .......................... A61F 2/95 623/1.11 |

(Continued)

FOREIGN PATENT DOCUMENTS

| CN | 201519366 U | 7/2010 |
| CN | 102218191 A | 10/2011 |

(Continued)

OTHER PUBLICATIONS

Extended European Search Report dated Aug. 4, 2021, in connection with corresponding EP Application No. 18876082.1; 5 pages.

(Continued)

*Primary Examiner* — Kathleen S Holwerda
*Assistant Examiner* — Serenity A Miller
(74) *Attorney, Agent, or Firm* — Maier & Maier, PLLC

(57) ABSTRACT

An implant delivery device includes a holder, a guide rod, and a sliding handle. One end of the guide rod is connected to the holder, and the other end of the guide rod penetrates the sliding handle. Multiple first engagement structures axially spaced apart from each other are disposed on an outer surface of the guide rod. The delivery device also includes a position locking device disposed in the sliding handle. The position locking device includes a tooth block) and an elastic component. The tooth block is sleeved on the guide rod and is provided with a second engagement structure. The elastic component and the tooth block cooperate to allow the first engagement structures and the second engagement structure to engage with each other allowing an implant to be in a release-locked state. These and other elements allow for the implant to be gradually released or release-locked.

14 Claims, 13 Drawing Sheets

(58) Field of Classification Search
CPC ........ A61F 2/9662; A61F 2/97; A61F 2/2427; A61F 2/2436; A61F 2002/9632; A61F 2002/9665; A61F 2/01–014; A61F 2002/015–018

See application file for complete search history.

(56) References Cited

U.S. PATENT DOCUMENTS

| | | | |
|---|---|---|---|
| 2009/0143738 A1* | 6/2009 | Hendriksen | A61F 2/95 604/165.01 |
| 2010/0094393 A1* | 4/2010 | Cordeiro | A61F 2/95 623/1.11 |
| 2013/0304189 A1 | 11/2013 | Shimoyama | |
| 2014/0336744 A1 | 11/2014 | Tani et al. | |
| 2016/0228274 A1 | 8/2016 | Longo et al. | |
| 2016/0338864 A1* | 11/2016 | Vad | A61F 2/9661 |

FOREIGN PATENT DOCUMENTS

| | | |
|---|---|---|
| CN | 102892389 A | 1/2013 |
| CN | 103028153 A | 4/2013 |
| CN | 105361985 A | 3/2016 |
| CN | 105832452 A | 8/2016 |
| CN | 106237491 A | 12/2016 |
| CN | 206102784 U | 4/2017 |

OTHER PUBLICATIONS

International Search Report dated Jan. 30, 2019 and Written Opinion in corresponding International application No. PCT/CN2018/113566; 12 pages.
Office Action dated Mar. 23, 2021, in connection with corresponding Chinese Application No. 201810837954.6 (25 pp., including machine-generated English translation).
Chinese Office Action dated Jul. 2, 2020, in connection with corresponding CN Application No. 201810837954.6 (25 pp., including machine-generated English translation).
Chinese Office Action dated Mar. 23, 2021, in connection with corresponding CN Application No. 201810837954.6 (28 pp., including machine-generated English translation).
Chinese Search Repod dated Mar. 23, 2021, in connection with corresponding CN Application No. 201810837954.6; 1 page.
Indian Office Action dated May 28, 2021, in connection with corresponding IN Application No. 202017020326; 5 pages.
Office Action dated May 4, 2022, in connection with corresponding EP Application No. 18876082.1, 4 pages.

* cited by examiner

DELIVERY DEVICE

FIELD

Embodiments relate to the field of medical instruments, and in particular to a delivery device with a release position locking function.

BACKGROUND

In recent years, interventional therapy for cardiovascular diseases has become an important means to cure patients. Interventional implants are classified into stents, occluders and other small medical devices implanted in human or animal bodies. Taking the stent as an example, with the continuous development of interventional techniques in the medical field, the advantages of using a covered stent in the treatment of aortic aneurysm and arterial dissection are increasingly prominent. The covered stent is an artificial blood vessel adaptive to the size of blood vessels and mainly includes a membrane and a stent supporting the membrane, where the membrane is generally made of terylene or e-PTFE membrane, and the supporting stent is mainly formed by weaving stainless steel wires or nickel-titanium alloy wires. When the covered stent is used, the covered stent is compressed into a lumen of a sheath of a stent delivery device. A blood vessel is generally punctured at a femoral artery or iliac artery position, and a guide wire is used for establishing a track, and the delivery device is used for establishing a conveying path through the iliac artery-abdominal aorta-thoracic aorta-aortic arch-ascending aorta, and then is transmitted to a specified position of a lesion, and then the covered stent is released. The covered stent is tightly attached to the wall of the arterial aneurysm after being released and extending, and the membrane of the covered stent isolates the blood flow from the lesion, so that the impact of the blood flow on the wall of the arterial aneurysm at the lesion is eliminated, and a channel for normal circulation of blood is established. Finally, the guide wire and the delivery device are withdrawn to realize the interventional treatment on the aortic aneurysm and arterial dissection.

A delivery device of an existing stent system generally includes a TIP head, a sheath core tube, a push rod, a sheath, a holder, a sliding handle and other components. A common stent release mode is that the stent is first conveyed to a pre-specified position of a hemangioma through the delivery device to be positioned, and then the sheath is withdrawn to release the stent until the stent is completely released and extends. However, after the pre-specified position of the hemangioma is positioned, the delivery device should cooperate with the stent for safe release so as to ensure that the stent is uniform and stable in the release process, so that the stent is gradually controllable in the release process to avoid stent displacement or stent release failure due to operator's unstable operation during the release process of the stent.

At the same time, for a clinic in which a number of stents are to be implanted simultaneously in a patient, it is necessary to operate another stent after the partial release of a prior stent is stopped. Thus, it is needed for a device that can effectively lock and control the release of a stent during the release of the stent so as to achieve gradual release of the stent, and meanwhile after the stent is partially released and extends, the release process of the stent can be position-locked and maintains a suspended state, and the whole stent system remains in a safe and effective state during the position—locked process. When the position-locked state of the stent release process is removed, the stent can also be released stepwise safely and effectively, i.e. the unreleased part of the stent can still be released.

SUMMARY

Therefore, embodiments herein provide a delivery device with a release position locking function in response to the need of position locking to interventional implants during a release process.

One embodiment includes delivery device for conveying an implant, including: a holder, a guide rod, a sliding handle and a position locking device;

where one end of the guide rod being connected to the holder, and the other end of the guide rod penetrating through the sliding handle;

where the outer surface of the guide rod is provided with a number of first engagement structures axially spaced apart from each other along the guide rod; where the position locking device is provided in the sliding handle, and the position locking device includes a tooth block and an elastic component, where the tooth block is sleeved on the guide rod, and the tooth block is provided with a second engagement structure; and the elastic component and the tooth block cooperate to allow the first engagement structures and the second engagement structure to engage with each other when the elastic component is not compressed or partially compressed, allowing the implant to be in a release-locked state; and the implant is in a releasable state when the elastic component is compressed until the first engagement structures and the second engagement structure are separated.

In one embodiment, the tooth block includes a U-shaped support member and a baffle connected to an open end of the support member, and the second engagement structure of the tooth block is provided on a surface of the baffle facing an inner side of the support member; and the first engagement structures of the guide rod surround the outer surface of the guide rod, or the first engagement structures of the guide rod are positioned on a part of the outer surface of the guide rod.

In one embodiment, the position locking device further includes a guide rod sleeve, and the guide rod sleeve is sleeved on the surface of the guide rod, and an opening is formed in a side wall of the guide rod sleeve, and both ends of the opening along the axial direction of the guide rod sleeve are respectively provided with a guide rail; two opposite sliding blocks are provided on the baffle, and the tooth block is sleeved on the surface of the guide rod sleeve, and the second engagement structure on the baffle corresponds to the opening, and the two sliding blocks on the baffle respectively penetrate through the two guide rails of the guide rod sleeve.

In one embodiment, the tooth block includes a U-shaped support member and a baffle connected to an open end of the support member, and the second engagement structure of the tooth block is provided on an inner wall of the support member; and the first engagement structures of the guide rod surround the outer surface of the guide rod, or the first engagement structures of the guide rod are positioned on a part of the outer surface of the guide rod.

In one embodiment, the position locking device further includes a guide rod sleeve, and the guide rod sleeve is sleeved on the surface of the guide rod, and two opposite guide rails are provided at the bottom of the guide rod sleeve along the axial direction, and one or two openings are provided on a side wall of the guide rod sleeve; two opposite sliding blocks are provided on the baffle, and the tooth block is sleeved on the surface of the guide rod sleeve, and the second engagement structure on the support member corresponds to the opening, and the two sliding blocks on the baffle respectively penetrate through the two guide rails of the guide rod sleeve.

In one embodiment, both ends of the guide rod sleeve are respectively provided with a first fixing member for connecting to the inner wall of the sliding handle.

In one embodiment, the position locking device further includes a key assembly, and the key assembly includes a key and a key support; one end of the key support is connected to the key, the other end thereof is connected to the top of the tooth block, or the other end thereof is connected to the top of the tooth block when the key assembly is pressed; when the key assembly is pressed, the elastic component is compressed.

In one embodiment, the elastic component is provided inside of the sliding handle at the top, and a transverse plate is provided inside of the sliding handle at the top, with an opening is provided on the transverse plate; and one end, close to the tooth block, of the key support penetrates through the opening and is connected to the tooth block; and the elastic component is sleeved on the periphery of the key support and is positioned between the key and the transverse plate.

In one embodiment, the elastic component is provided inside the sliding handle, and one end of the elastic component is connected to the tooth block and the other end of the elastic component is connected to the inner wall of the sliding handle at the bottom.

In one embodiment, another elastic component is further provided inside of the sliding handle at the top; and another elastic component is sleeved on the periphery of the key support, and is positioned between the key assembly and the tooth block.

In one embodiment, the top of the sliding handle is provided with an opening which the key passes through or fills.

In one embodiment, the key assembly is provided with at least one second fixing member; when the key assembly is not pressed, the second fixing member abuts against the inner side edge of the opening at the top of the sliding handle.

In one embodiment, the number of the first engagement structures axially spaced apart from each other along the guide rod are provided parallel to one another and equidistantly spaced.

In one embodiment, the first engagement structures are perpendicular to an axial direction of the guide rod.

In one embodiment, the guide rod has a chute extending in an axial direction thereof, and the first engagement structures are positioned on outer surface of the guide rod adjacent to both sides of the chute.

By adopting the position locking device with such structure in the delivery device, when the elastic component is compressed until the first engagement structures and the second engagement structure which are engaged together before are separated from each other, the delivery device can release the constraining force on the sliding handle from sliding axially along the guide rod, so that the implant can be gradually released or recovered according to the axial sliding of the sliding handle; and when the elastic component is reset, the first engagement structures and the second engagement structure are engaged, so that the sliding handle is locked, and the release of the implant is suspended. Therefore, the delivery device has a release position locking function, so that the implant can be safely and effectively released gradually and locked in time.

DETAILED DESCRIPTION OF EMBODIMENTS

In order to make the purposes, technical solutions, and advantages of the embodiments more fully apparent, further details of the disclosure are set forth with reference to the accompanying drawings and embodiments. It can be appreciated that the embodiments described herein are merely illustrative and are not intended to be limiting. In the field of interventional medical devices, after implanting the delivery device into a blood vessel, it is defined that the end of the delivery device closest to an operator is a proximal end and the end of the delivery device furthest from the operator is a distal end. Similarly, the proximal and distal ends of the various components in the delivery device are defined in accordance with this principle.

The delivery device in the embodiments may be used for, but is not limited to, delivery of interventional implants such as stents, occluders and the like, and the structure and function of the delivery device will be described in detail herein by way of example of a stent. The embodiments relate to a stent which is a covered stent, where the covered stent refers to a structure after a film is covered on the surface of a bare stent, and the bare stent refers to a structure which includes a number of waveform rings without film between the waveform rings.

Embodiment 1

Figure 1:
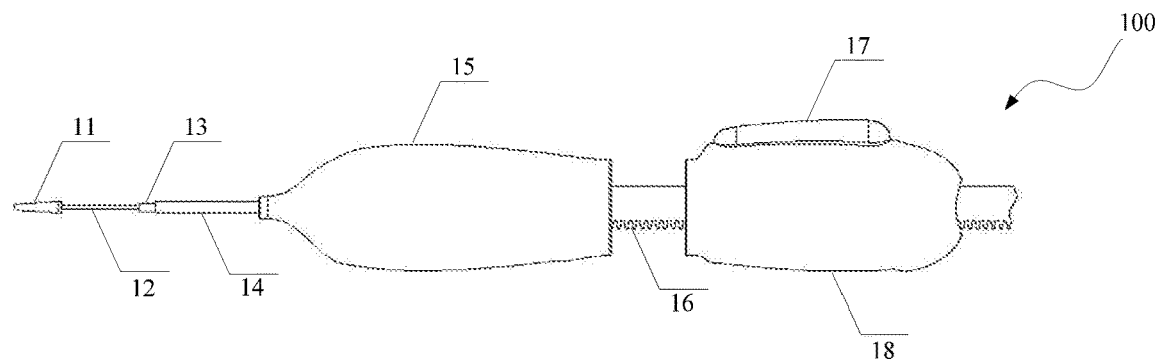
FIG. 1 is a structural schematic diagram of a delivery device according to Embodiment 1.

Referring to FIG. 1, there is shown a structural schematic diagram of a delivery device 100 in an embodiment. The delivery device 100 includes a sheath core tube 12, a push rod 13, a sheath 14, a guide rod 16, an end head 11, a holder 15, a sliding handle 18 and a position locking device 17, where the sheath core tube 12, the push rod 13, the sheath 14 and the guide rod 16 are coaxially sleeved from inside to outside, and the end head 11 is provided at the distal end of the sheath core tube 12, and the holder 15 is connected to the distal end of the guide rod 16, and the sliding handle 18 is sleeved on the guide rod 16, and the position locking device 17 is at least partially received inside the sliding handle 18.

The end head 11 and the sheath core tube 12 are both members with a cavity inside. The end head 11 can be a TIP head, and the end head 11 and the distal end of the sheath core tube 12 are fixedly integrated into a passage of a guide wire, so that the delivery device 100 with the guide wire can smoothly enter a blood vessel under the guide of the guide wire. The push rod 13 is a tubular member, and the proximal end of the push rod 13 is fixedly connected to the proximal end of the sheath core tube 12, and the inner diameter of the push rod 13 is larger than the outer diameter of the sheath core tube 12. As the sheath core tube 12 slides axially, the push rod 13 slides synchronously with the sheath core tube 12.

The sheath 14 is a member which is sleeved on the outer edge of the push rod 13 and can slide axially with respect to the push rod 13. When the distal end of the sheath 14 is in contact with the proximal end of the end head 11, the sheath 14, the sheath core tube 12 and the distal end face of the push rod 13 cooperate to form a space for receiving a stent, and the proximal end of the stent (not shown) abuts against the distal end face of the push rod 13, and the distal end face of the push rod 13 limits the axial movement of the stent during the release of the stent. Since the distal end of the guide rod 16 is fixedly connected to the proximal end of the holder 15, and the sliding handle 18 penetrates through the guide rod 16 at the proximal end of the guide rod 16, the sliding handle 18 can move axially relative to the holder 15 along the guide rod 16. When the sliding handle 18 is closed towards the holder 15, a part of the sheath core tube 12 between the push rod 13 and the end head 11 is exposed outside the push rod 13, and the exposed length is the effective length of the stent after compression, i.e. the maximum distance that the sliding handle 18 moves away from the holder 15.

When the sliding handle 18 is pulled proximally, the sheath 14 is withdrawn, and the stent loses the constraint from the sheath 14 and is released and extends.

The holder 15 is of a housing construction and is a fixed member of the delivery device 100 in order to facilitate gripping by a surgeon during a clinical procedure, so that the delivery device 100 is in a stable condition as a whole. The sheath core tube 12 and the push rod 13 extend through the holder 15 and the sliding handle 18. The guide rod 16 is a guide mechanism for axial release of the stent, the distal end of which is fixed in the holder 15, and the proximal end of which passes out of the sliding handle 18. The sliding handle 18 is sleeved on the guide rod 16 and is integral with the proximal end of the sheath 14. For example, the proximal end of the sheath 14 is fixed within the sliding handle 18, the distal end of which passes out of the holder 15. The sliding handle 18 can slide along the axial direction of the guide rod 16 to drive the sheath 14 to slide, so that the stent can be released and extend by withdrawing the sheath 14.

Figure 2:
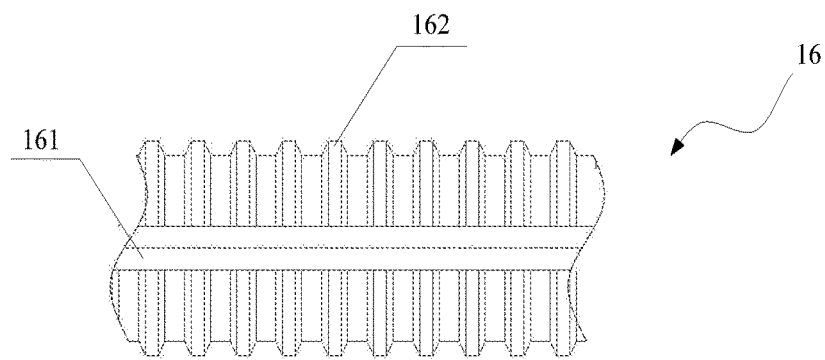
FIG. 2 is a structural schematic diagram of a guide rod of the delivery device according to Embodiment 1.

As shown in FIG. 2, the outer surface of the guide rod 16 is provided with a number of first engagement structures 162 axially spaced apart from each other along the guide rod 16, and the inside of the guide rod 16 is a cavity. Further, the outer surface of the guide rod 16 is provided with at least one chute 161 extending in the axial direction of the guide rod 16, and the chute 161 is communicated with the cavity inside the guide rod 16. Further, the first engagement structures 162 are positioned on the outer surface of the guide rod 16 adjacent to both sides of the chute 161. Further, the number of first engagement structures 162 provided on the outer surface of the guide rod 16 are provided parallel to one another and equidistantly spaced. Further, the first engagement structures 162 are perpendicular to an axial direction of the guide rod 16. The first engagement structures 162 may be a toothed structure, or may be any other structure capable of effecting engagement.

The sliding handle 18 is connected to the proximal end of the sheath 14 by a connecting member (not shown) provided in the chute 161, and the position locking device 17 can be placed wholly inside the sliding handle 18 or partly inside the sliding handle 18. Further, the top of the sliding handle 18 is provided with an opening at which the top of the position locking device 17 can protrude, as shown in the position of FIG. 1. In another embodiment, the opening may be covered by a layer of flexible membrane on the sliding handle, and the size of the flexible membrane is adapted to the size of the opening, in which case the position locking device 17 is considered to be entirely positioned inside the sliding handle 18. When the sliding handle 18 slides axially along the guide rod 16, the sheath 14 and the position locking device 17 slide synchronously with the sliding handle 18.

Figure 3:
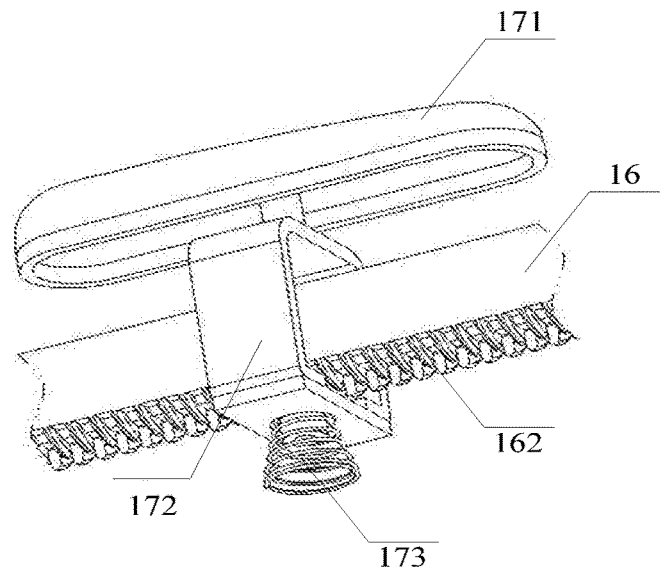
FIG. 3 is a structural schematic diagram of a position locking device of the delivery device according to Embodiment 1.

For example, as shown in FIG. 3, the position locking device 17 includes a key assembly 171, a tooth block 172 and an elastic component 173, and the tooth block 172 is sleeved on the outer side of the guide rod 16, and the elastic component 173 is provided inside the sliding handle 18. One end of the elastic component 173 is connected to the tooth block 172, and the other end of the elastic component 173 is connected to the inner wall of the sliding handle 18 at bottom. The inside of the tooth block 172 is provided with at least one second engagement structure 1721 (referring to FIG. 4(a)). The position locking device 17 is used for driving the tooth block 172 to compress the elastic component 173 when the key assembly 171 is pressed, so that the first engagement structures 162 of the guide rod 16 and the second engagement structure 1721 of the tooth block 172 which are engaged together are separated from each other, and the constraining force of the axial movement of the sliding handle 18 is eliminated; and when the key assembly 171 is released, the elastic component 173 returns to act on the tooth block 172, so that the first engagement structures 162 of the guide rod 16 are engaged with the second engagement structure 1721 of the tooth block 172 so as to realize the position locking of the sliding handle 18. It may be noted that when the key assembly 171 is pressed and the first engagement structures 162 are not separated from the second engagement structure 1721, the elastic component 173 is in a partially compressed state, and since the first engagement structures 162 are still partially engaged with the second engagement structure 1721, the stent is still in a release-locked state; when the key assembly 171 is pressed and the elastic component 173 is compressed until the first engagement structures 162 are separated from the second engagement structure 1721, the stent is in a releasable state.

Figure 4:
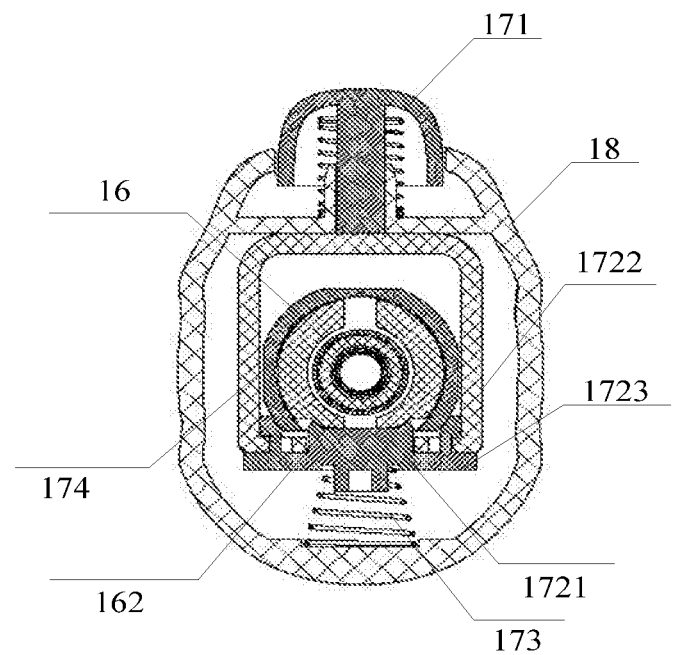
FIG. 4(a) is a structural schematic diagram of the position locking device in a sliding handle under a position-locked state of a stent in the delivery device of Embodiment 1.
FIG. 4(b) is a structural schematic diagram of the position locking device in a sliding handle under a position-locked state of a stent in the delivery device of Embodiment 1.
FIG. 4(c) is a structural schematic diagram of the position locking device in the sliding handle under the release-unlocked state of the stent in the delivery device according to Embodiment 1.
FIG. 4(d) is a structural schematic diagram of the position locking device in the sliding handle under the release-unlocked state of the stent in the delivery device according to Embodiment 1.
Figure 4:
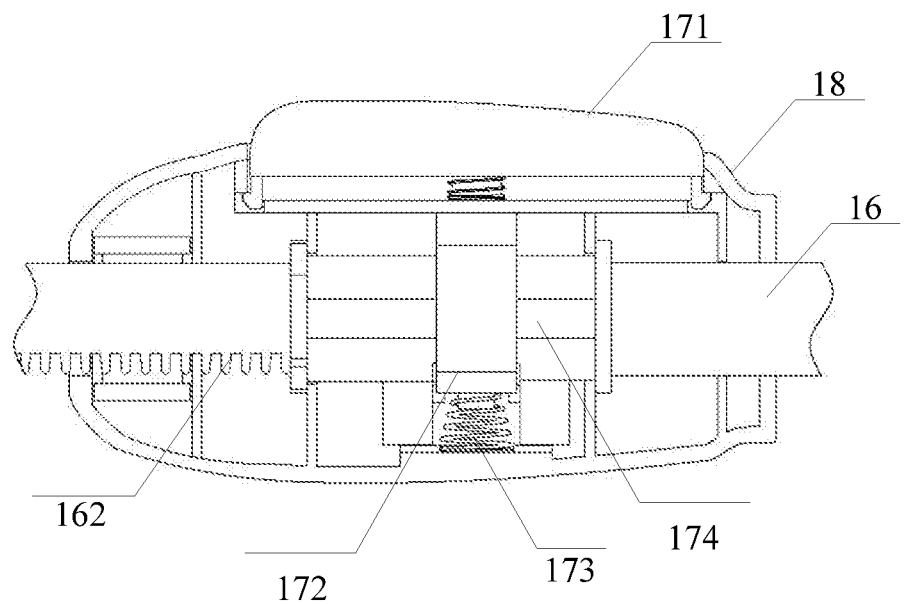
Figure 4:
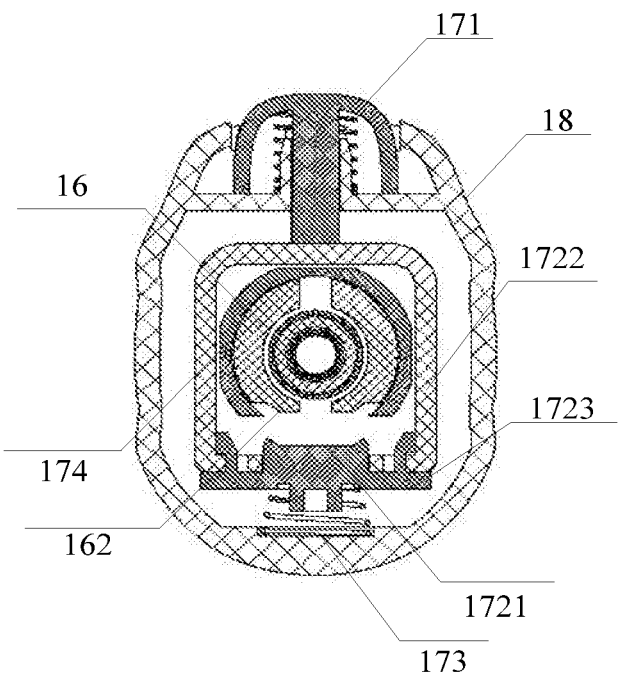
Figure 4:
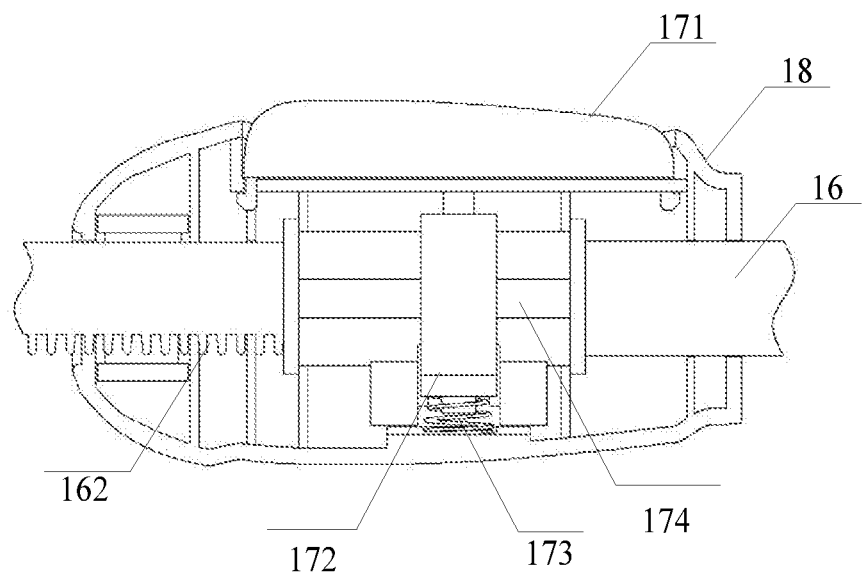

In the embodiment, one end of the elastic component 173 is connected to the bottom of the tooth block 172, and the other end thereof is connected to the inner wall of the sliding handle 18 in an unrestricted manner. Referring also to FIGS. 4(a)-4(b), when the key assembly 171 is not pressed, the second engagement structure 1721 on the tooth block 172 is engaged with the first engagement structures 162 on the guide rod 16 under the support of the elastic component 173, where upon the axial movement of the sliding handle 18 is constrained by this engagement, i.e. the sliding handle 18 cannot slide axially along the guide rod 16, thereby realizing the position locking of the stent in the current release state. Referring to FIGS. 4(c)-4(d), when the key assembly 171 is pressed, the key assembly 171 pushes the tooth block 172 to move towards the bottom of the sliding handle 18 by the pressing force, thereby compressing the elastic component 173, where upon the second engagement structure 1721 on the tooth block 172 moves away from the first engagement structures 162 on the guide rod 16 until the first engagement structures 162 are completely disengaged from the second engagement structure 1721, the constraining force on the axial movement of the sliding handle 18 is released, i.e., the sliding handle 18 can slide axially along the guide rod 16, thereby effecting the gradual release of the stent.

Figure 5:
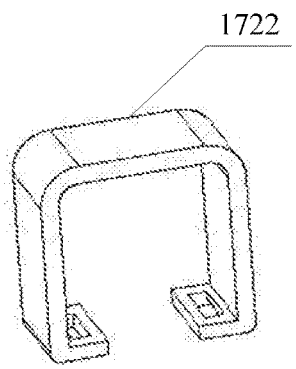
FIG. 5(a) is a structural schematic diagram of a support member of a tooth block of the delivery device according to Embodiment 1.
FIG. 5(b) is a structural schematic diagram of a baffle of the tooth block of the delivery device according to Embodiment 1.
Figure 5:
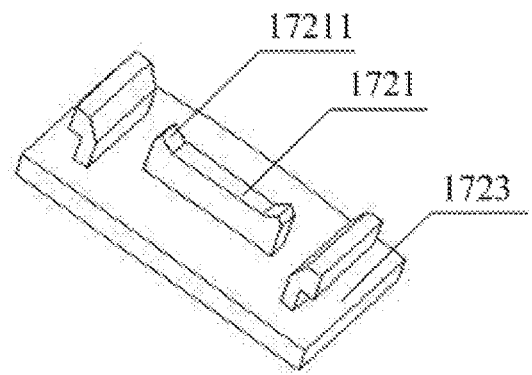

Further, referring collectively to FIGS. 5(a)-5(b), the tooth block 172 includes a U-shaped support member 1722 and a baffle 1723 connected to an open end of the support member 1722, and the second engagement structure 1721 of the tooth block 172 is provided on a surface of the baffle 1723 facing the inside of the support member 1722; and the first engagement structures 162 of the guide rod 16 surround the outer surface of the guide rod 16, or the first engagement structures 162 of the guide rod 16 are positioned on a portion of the outer surface of the guide rod 16. Further, the first engagement structures 162 of the guide rod 16 are positioned on both sides of one of the chutes 161 of the guide rod 16, and the length of the first engagement structures 162 of the guide rod 16 is adapted to the length of the second engagement structure 1721 of the tooth block 172. The baffle 1723 may have a square configuration.

It can be appreciated that the support member 1722 may also be an arc body whose opening is the same as the length of the baffle 1723 in FIG. 5(b), and whose distance between the opening and the top is the same as that between the opening and top of the support member 1722 in FIG. 5(a). Further, the baffle 1723 may be an arc body having a certain radian at both ends and a length corresponding to the size of the opening of the support member 1722. The second engagement structure 1721 on the tooth block 172 may be provided in a number according to the length or width of the tooth block 172, and the teeth 17211 on the second engagement structure 1721 may be provided in any number. Referring to collectively FIGS. 5(a)-5(b), the support member 1722 may be connected to the baffle 1723 in a manner that is not limited to structural fixed connection, bolted connection, metal welding, adhesive connection, and the like, in addition to a snap connection.

By adopting the position locking device 17 of the delivery device 100 according to this embodiment, when the key assembly 171 is pressed, it the position locking device 17 drives the tooth block 172 to compress the elastic component 173 so that the second engagement structure 1721 on the tooth block 172 and the first engagement structures 162 on the guide rod 16 which are originally engaged together are separated from each other, thereby releasing the constraining force of the sliding handle 18 from sliding axially along the guide rod 16, so that the stent can be gradually released or recovered according to the axial sliding of the sliding handle 18; and when the key assembly 171 is released, the tooth block 172 is driven to move towards the direction close to the key assembly 171 by the return of the elastic component 173, so that the second engagement structure 1721 on the tooth block 172 and the first engagement structures 162 on the guide rod 16 are restored to the engagement state to generate a constraining force on the sliding handle 18 from sliding axially along the guide rod 16, namely, the sliding handle 18 is locked at the current position and the release of the stent is then suspended.

It can be appreciated that in other embodiments, the key assembly 171 may be omitted and the support member 1722 of the tooth block 172 may protrude at least partially from the sliding handle 18, and the elastic component 173 may be compressed or reset by pressing or releasing the support member 1722.

Embodiment 2

Figure 6:
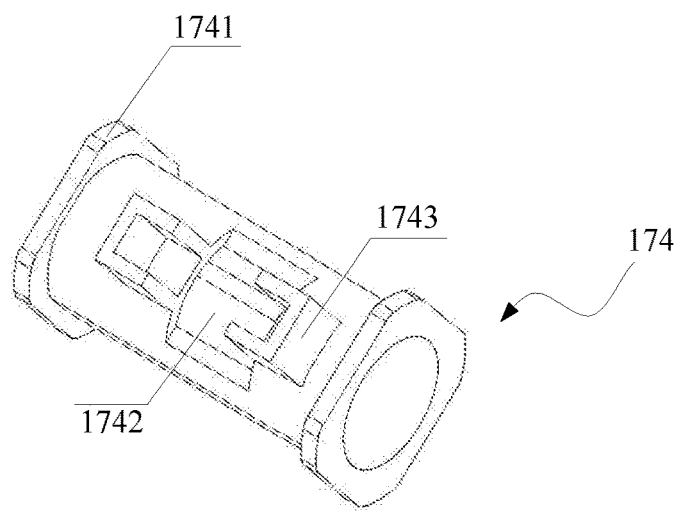
FIG. 6(a) is a structural schematic diagram of a guide rod sleeve of the delivery device according to Embodiment 2.
FIG. 6(b) is a structural schematic diagram of a baffle of the delivery device according to Embodiment 2.
FIG. 6(c) is a schematic diagram showing the connection of the guide rod sleeve and the position locking device of the delivery device according to Embodiment 2.
Figure 6:
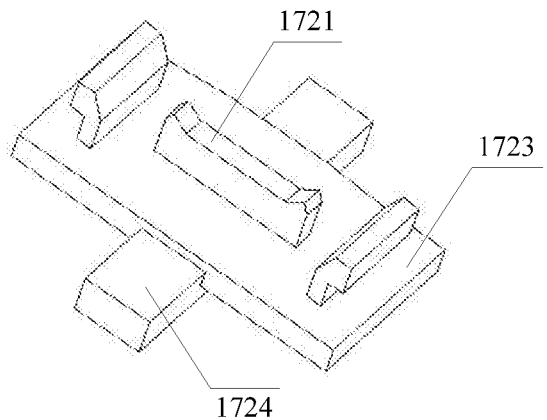
Figure 6:
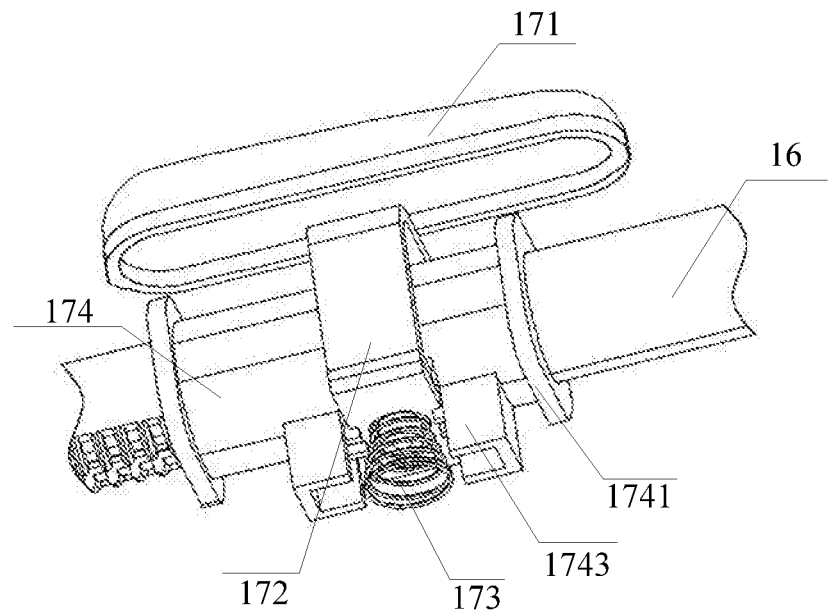

Embodiment 2 differs from Embodiment 1 in that the position locking device 17 of Embodiment 2 may further include a guide rod sleeve 174 (shown in FIG. 6(a)) having a hollow interior and open at both ends, and the baffle 1723 is provided with two opposing sliding blocks 1724 (shown in FIG. 6(b)). Referring to FIGS. 6(a)-6(c), the guide rod sleeve 174 is sleeved on the surface of the guide rod 16, an opening 1742 is provided on a side wall of the guide rod sleeve 174, and both ends of the opening 1742 in the axial direction of the guide rod sleeve 174 are respectively provided with a guide rail 1743; the tooth block 172 is sleeved on the surface of the guide rod sleeve 174 and the second engagement structure 1721 on the baffle 1723 corresponds to the opening 1742 of the guide rod sleeve 174 such that the second engagement structure 1721 can pass through the opening 1742 to be engaged with the first engagement structures 162 of the guide rod 16. The two sliding blocks 1724 on the baffle 1723 pass through the two guide rails 1743 of the guide rod sleeve 174, respectively. Further, the openings at both ends of the guide rod sleeve 174 are respectively provided with a first fixing member 1741 for fixedly connecting to the inner wall of the sliding handle 18.

It can be appreciated that in other embodiments, the first fixing member 1741 may be omitted, so long as a connection structure capable of being connected to the inner wall of the sliding handle 18 may be provided at other portions of the surface of the guide rod sleeve 174.

The guide rod sleeve 174 is a member which can be sleeved on the outer surface of the guide rod 16 and can slide axially and synchronously with the sliding handle 18 along the guide rod 16, where two first fixing members 1741 of the guide rod sleeve 174 are fixedly connected to the proximal end and the distal end of the sliding handle 18, respectively, inside the sliding handle 18. The opening 1742 of the guide rod sleeve 174 enables at least one first engagement structure 162 on the surface of the guide rod 16 to appear within the opening 1742 and enables the second engagement structure 1721 on the tooth block 172 to pass through the opening 1742 and be engaged with the first engagement structures 162 on the guide rod 16 when the key assembly 171 is not pressed. The length and width of the opening 1742 may depend on the area occupied by all of the second engagement structures 1721 on the baffle 1723.

The shape of the sliding blocks 1724 may be square, may be cylindrical, or any other shape, as desired, with the shape and size depending on the shape and size of the accommodation space of the guide rails 1743. The opposite sides of the two guide rails 1743 are provided with openings, and further, one side of the two guide rails 1743 facing outwards in the radial direction of the guide rod sleeve 174 may be provided with openings, as shown in FIG. 6(a). The guide rails 1743 function to slide the two sliding blocks 1724 of the tooth block 172 along the two guide rails 1743, respectively, so that the second engagement structure 1721 on the tooth block 172 can be smoothly engaged with or disengaged from the first engagement structures 162 on the guide rod 16.

According to the delivery device in Embodiment 2, the guide rod sleeve 174 is additionally provided in the position locking device 17, so that other components in the position locking device 17 are more fixed in position under the cooperation of the guide rod sleeve 174 and not easy to deviate when moving, and can slide steadily with the guide rod sleeve 174 in sync with the sliding handle, and therefore the stability of the stent release can be guaranteed.

Embodiment 3

Figure 7:
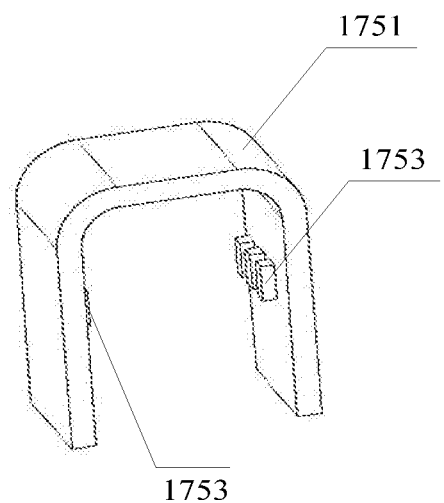
FIG. 7(a) is a structural schematic diagram of a support member with second engagement structures provided on the left and right sides thereof in the tooth block of the delivery device according to Embodiment 3.
FIG. 7(b) is a structural schematic diagram of a baffle of the tooth block of the delivery device according to Embodiment 3.
FIG. 7(c) is a structural schematic diagram of the support member with a second engagement structure provided on one side thereof in the tooth block of the delivery device according to Embodiment 3.
Figure 7:
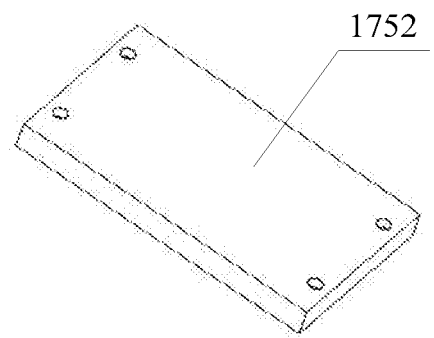
Figure 7:
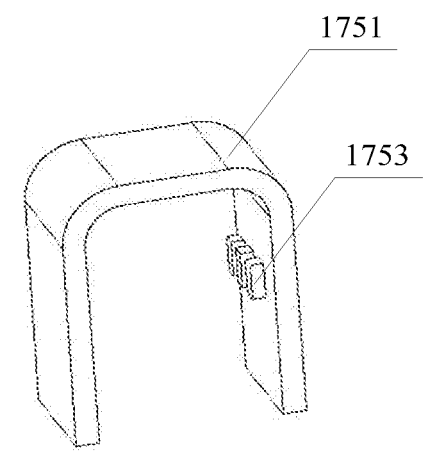

Embodiment 3 differs from Embodiment 1 in that the delivery device of Embodiment 3 includes a different tooth block 175 from the tooth block 172 of Embodiment 1. Accordingly, the first engagement structures 163 on the guide rod 16 of this embodiment differ from the first engagement structures 162 of Embodiment 1. Referring collectively to FIGS. 7(a)-7(b), in this embodiment, the tooth block 175 is generally a hollow cuboid and includes a U-shaped support member 1751 and a baffle 1752 connected to an open end of the support member 1751. The support member 1751 includes a base plate and two side plates respectively connected to both ends of the base plate. The second engagement structures 1753 of the tooth block 175 are provided on the inner side walls of the two side plates of the support member 1751 or on the inner side wall of only one of the side plates. The number of first engagement structures 163 of the guide rod 16 surround the outer surface of the guide rod 16, and the number of first engagement structures 163 are engaged with the number of second engagement structures 1753 on the two side plates of the support member 1751. Alternatively, the first engagement structures 163 of the guide rod 16 are only positioned on a part of the outer surface of the guide rod 16, and the first engagement structures 163 are engaged with the second engagement structures 1753 on one of the side plates of the support member 1751. It can be appreciated that the provision of the second engagement structures 1753 of the tooth block 175 on only one of the side plates of the support member 1751 also enables the position locking and unlocking of the sliding handle 18. Referring to FIG. 7(c), FIG. 7(c) is a structural schematic diagram of the second engagement structures 1753 of the tooth block 175 provided on only one of the side plates of the support member 1751.

It can be appreciated that the support member 1751 may also be an arc body whose opening is the same as the length of the baffle 1752 in FIG. 7(b), and whose distance between the opening and the top is the same as that between the opening and the top of the support member 1751 in FIG. 7(a). Further, the baffle 1752 may be an arc body having a certain radian at both ends and a length corresponding to the size of the opening of the support member 1751. The second engagement structures 1753 on the tooth block 175 may be provided in a number according to the length or width of the tooth block 175, and the teeth (not shown) on the second engagement structures 1753 may be provided in rectangular or cylindrical structures whose size corresponds to the gap of the adjacent first engagement structures 163 on the guide rod 16. The support member 1751 may be connected to the baffle 1752 in a manner that is not limited to structural fixed connection, bolted connection, metal welding, adhesive connection, snap connection and the like. It may be appreciated that the body structure of the tooth block 175 may be configured as a solid structure or a hollow structure.

Figure 8:
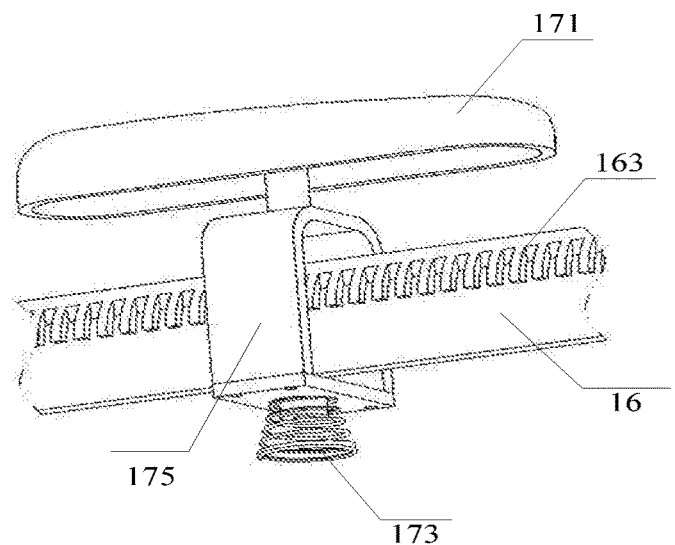
FIG. 8 is a structural schematic diagram of a position locking device of the delivery device according to Embodiment 3.
Figure 9:
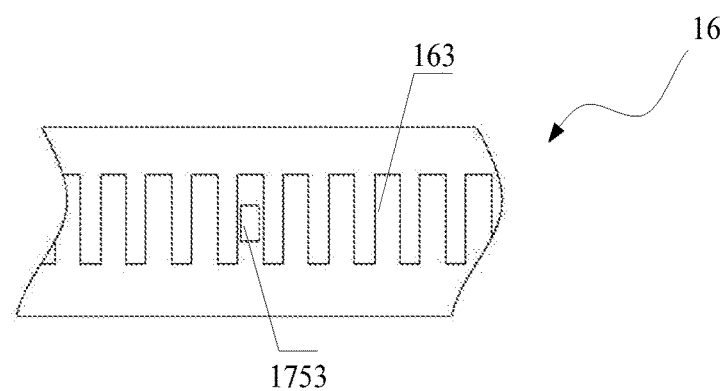
FIG. 9(a) is a schematic diagram of engaging the first engagement structure and the second engagement structure in the delivery device according to Embodiment 3.
FIG. 9(b) is a schematic diagram of the separation of the first engagement structure and the second engagement structure in the delivery device according to Embodiment 3.
Figure 9:
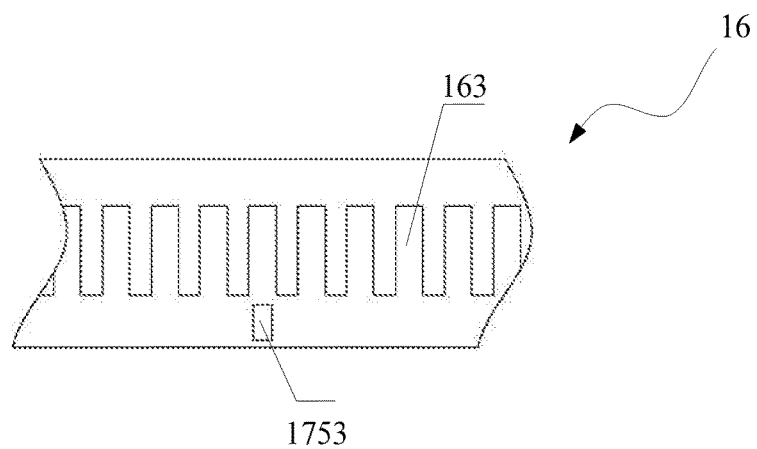

In the embodiment, as shown in FIG. 8, the position locking device 17 includes a key assembly 171, a tooth block 175 sleeved outside the guide rod 16, and an elastic component 173 provided at the bottom of the tooth block 175, where at least one second engagement structure 1753 is provided inside the tooth block 175 (referring to FIG. 7(a)). The position locking device 17 is used for driving the tooth block 175 to compress the elastic component 173 when the key assembly 171 is pressed, so that the first engagement structures 163 of the guide rod 16 and the second engagement structure 1753 of the tooth block 175 engaged together are separated from each other, and the constraining force of the axial movement of the sliding handle 18 is eliminated; and when the key assembly 171 is released, the first engagement structures 163 of the guide rod 16 are engaged with the second engagement structure 1753 of the tooth block 175 by the support force of the elastic component 173 acting on the tooth block 175 by returning so as to realize the position locking of the sliding handle 18. As shown in FIGS. 9(a)-9(b), FIGS. 9(a)-9(b) are schematic diagrams of engagement and separation of the first engagement structures 163 and the second engagement structure 1753, respectively.

One end of the elastic component 173 is connected to the bottom of the tooth block 175, and the other end thereof is connected to the inner wall of the sliding handle 18 in an unrestricted manner. Referring to FIGS. 10(a)-10(b), when the key assembly 171 is not pressed, the second engagement structure 1753 on the tooth block 175 is engaged with the first engagement structures 163 on the guide rod 16 under the support of the elastic component 173, in which case the axial movement of the sliding handle 18 is constrained by the engagement, that is, the sliding handle 18 cannot slide axially along the guide rod 16, thereby realizing the position locking of the stent in the current release state. Referring to FIGS. 10(c)-10(d), when the key assembly 171 is pressed, the key assembly 171 pushes the tooth block 175 to move towards the bottom of the sliding handle 18 by the pressing force, thereby compressing the elastic component 173, where upon the second engagement structure 1753 on the tooth block 175 moves away from the first engagement structures 163 on the guide rod 16 until the first engagement structures 163 are completely disengaged from the second engagement structure 1753, so that the constraining force on the axial movement of the sliding handle 18 is released, i.e., the sliding handle 18 can slide axially along the guide rod 16, thereby achieving the gradual release of the stent.

It can be appreciated that at least one second engagement structure 1753 may be provided on only one of the side plates of the support member 1751 of the tooth block 175, and accordingly, the first engagement structures 163 of the guide rod 16 may need to be provided on the side of the guide rod 16 that is in contact with the side plates of the support member 1751.

With the adoption of the position locking device 17 of such structure, when the key assembly 171 is pressed, the position locking device 17 of the delivery device according to Embodiment 3 drives the tooth block 175 to compress the elastic component 173, so that the second engagement structure 1753 on the tooth block 175 and the first engagement structures 163 on the guide rod 16 which are originally engaged together are separated from each other, thereby releasing the constraining force of the sliding handle 18 from sliding axially along the guide rod 16, and further the stent can be gradually released or recovered according to the axial sliding of the sliding handle 18; and when the key assembly 171 is released, the tooth block 175 is driven to move towards the direction close to the key assembly 171 by the return of the elastic component 173, so that the second engagement structure 1753 on the tooth block 175 and the first engagement structures 163 on the guide rod 16 are restored to the engagement state to generate a constraining force on the sliding handle 18 from sliding axially along the guide rod 16, namely, the sliding handle 18 is locked at the current position, and the release of the stent is then suspended.

Embodiment 4

Taking the case where both side plates of the support member 1751 are provided with the second engagement structures 1753, Embodiment 4 differs from Embodiment 3 in that the position locking device 17 in Embodiment 4 can further include a guide rod sleeve 176 (as shown in FIG. 11(a)) which is hollow inside and open at both ends, and the baffle 1752 is provided with two opposite sliding blocks 1754 (as shown in FIG. 11(b)). Referring collectively to FIGS. 11(a)-11(c), the guide rod sleeve 176 is sleeved on the surface of the guide rod 16, two opposite guide rails 1762 are provided at the bottom of the guide rod sleeve 176 (i.e., the end of the guide rod sleeve 176 opposite the baffle 1752) in the axial direction, and one or two openings 1763 are provided on the side wall of the guide rod sleeve 176. Further, one or two openings 1763 are formed in the side wall of the guide rod sleeve 176 perpendicular to the plane of the two opposite guide rails 1762; the tooth block 175 is sleeved on the surface of the guide rod sleeve 176, and the second engagement structure 1753 on the support member 1751 corresponds to the openings 1763 of the guide rod sleeve 176, and the two sliding blocks 1754 on the baffle 1752 respectively penetrate through the two guide rails 1762 on the guide rod sleeve 176. Further, both ends of the guide rod sleeve 176 are respectively provided with a first fixing member 1761 for fixedly connecting to the inner wall of the sliding handle 18.

The guide rod sleeve 176 is a member which can be sleeved outside the guide rod 16 and can slide axially and synchronously with the sliding handle 18 along the guide rod 16, where the two first fixing members 1761 of the guide rod sleeve 176 are fixedly connected to the proximal and distal ends of the sliding handle 18, respectively. The openings 1763 of the guide rod sleeve 176 enable at least one first engagement structure 163 on the surface of the guide rod 16 to be seen within the openings 1763 and enable the second engagement structures 1753 on the tooth block 175 to pass through the openings 1763 and be engaged with the first engagement structures 163 on the guide rod 16 when the key assembly 171 is not pressed. The length and width of the openings 1763 may depend on the area occupied by all of the second engagement structures 1753 on the support member 1751. When the two side plates of the support member 1751 are provided with the second engagement structures 1753, the side wall of the guide rod sleeve 176 is correspondingly provided with two openings 1763; when only one side plate of the support member 1751 is provided with the second engagement structure 1753, the side wall of the guide rod sleeve 176 is correspondingly provided with only one opening 1763.

Figure 11:
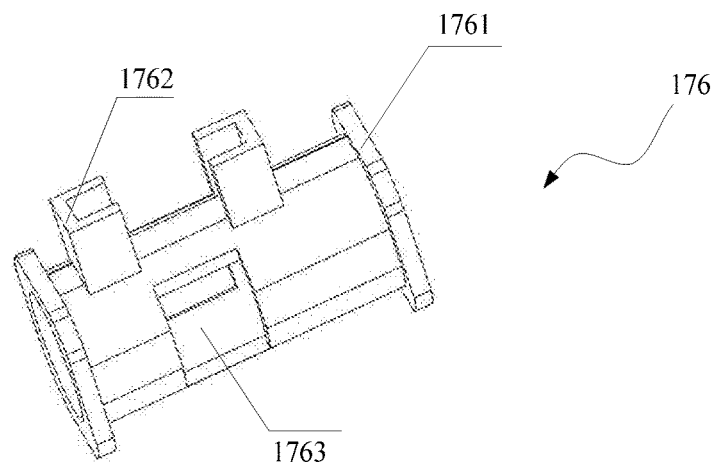
FIG. 11(a) is a structural schematic diagram of a guide rod sleeve of the delivery device according to Embodiment 4.
FIG. 11(b) is a structural schematic diagram of a baffle of the tooth block of the delivery device according to Embodiment 4.
FIG. 11(c) is a schematic diagram showing the connection of the guide rod sleeve and the position locking device of the delivery device according to Embodiment 4.
Figure 11:
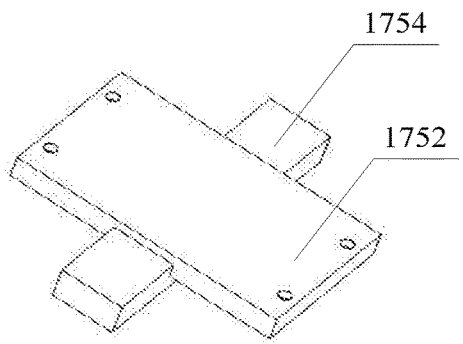
Figure 11:
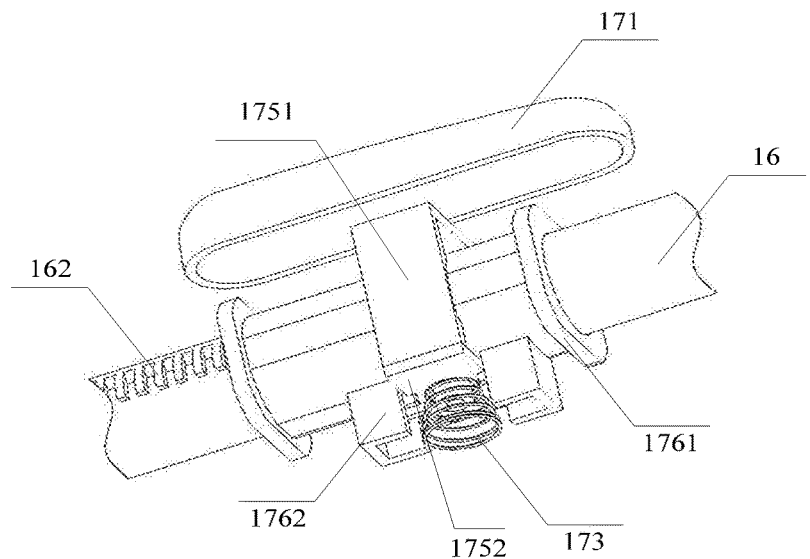

The shape of the sliding blocks 1754 may be square or cylindrical and so on, as desired, with the shape and size depending on the shape and size of the accommodation space of the guide rails 1762. The face-to-face sides of the two guide rails 1762 are provided with openings. Further, one side of each of the two guide rails 1762 facing outwards in the radial direction of the guide rod sleeve 176 may be provided with opening, as shown in FIG. 11(*a*). The guide rails 1762 function to slide the two sliding blocks 1754 of the tooth block 175 along the two guide rails 1762, respectively, so that the second engagement structures 1753 on the tooth block 175 can be smoothly engaged with or disengaged from the first engagement structures 163 on the guide rod 16.

According to the delivery device in Embodiment 4, the guide rod sleeve 176 is additionally provided in the position locking device 17, so that other components in the position locking device 17 are more fixed in position under the cooperation of the guide rod sleeve 176 and not easy to deviate when moving, and can slide steadily with the guide rod sleeve 176 in sync with the sliding handle, therefore the stability of the stent release can be guaranteed.

Embodiment 5

Figure 12:
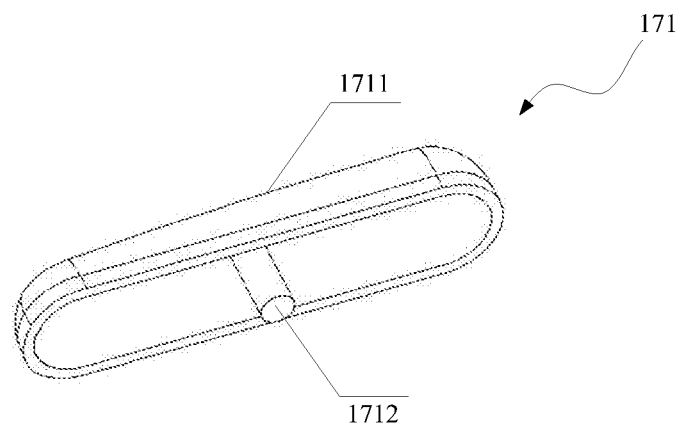
FIG. 12 is a structural schematic diagram of a key of the delivery device according to Embodiment 5.

In Embodiment 5, as shown in FIG. 12, the key assembly 171 of the delivery device includes a key 1711 and a key support 1712, one end of the key support 1712 is connected to the key 1711, and the other end thereof is connected to the top of the tooth block 172 (or the tooth block 175), or the other end thereof is connected to the top of the tooth block 172 (or the tooth block 175) when the key assembly 171 is pressed. The key support 1712 serves to drive the tooth block 172 (or the tooth block 175) to compress the elastic component 173 when the key assembly 171 is pressed. The key 1711 is hollow inside, and the key support 1712 is provided in the middle of the inner wall of the key 1711. One end of the key support 1712 is fixedly connected to the inner wall of the key 1711, and the other end thereof is fixedly connected to the tooth block 172 (or the tooth block 175). The key support 1712 may be cylindrical or rectangular and so on in configuration.

Embodiment 6

In Embodiment 6, the top of the sliding handle 18 is provided with an opening which the key 1711 passes through or fills.

An opening sized to just housing the key 1711 is provided at the top of the sliding handle 18, and the key 1711 can pass through the opening from inside the sliding handle 18 and partially protrude outside the sliding handle 18, or the key 1711 can fill the opening upwards from inside the sliding handle 18 so that the top of the key 1711 can be flush with the opening.

An advantage of providing such an opening at the top of the sliding handle 18 is that it is convenient for the operator to clearly identify the key assembly 171 and to lock the position of the sliding handle 18 by the key assembly 171, so as to achieve gradual release or timely locking of the stent.

Embodiment 7

Figure 10:
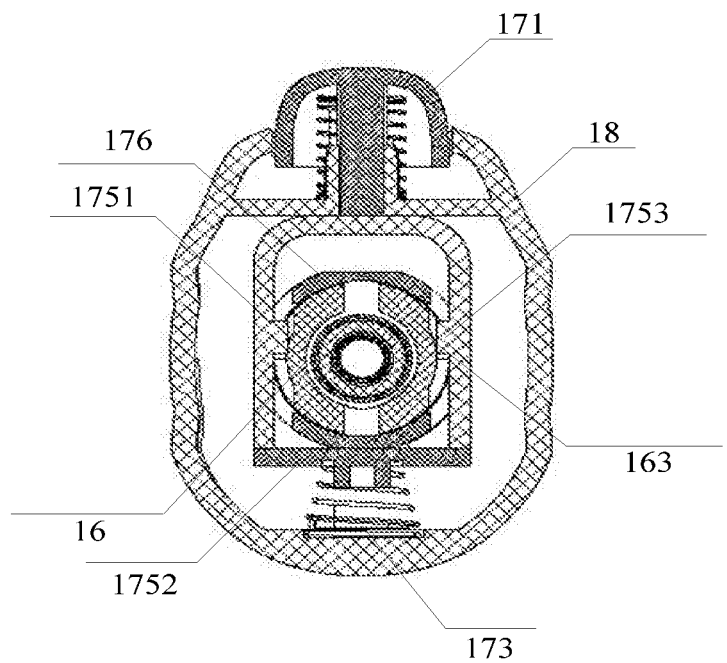
FIG. 10(a) is a structural schematic diagram of the position locking device in a sliding handle under the position-locked state of a stent in the delivery device according to Embodiment 3.
FIG. 10(b) is a structural schematic diagram of the position locking device in a sliding handle under the position-locked state of a stent in the delivery device according to Embodiment 3.
FIG. 10(c) is a structural schematic diagram of the position locking device in the sliding handle under the release-unlocked state of the stent in the delivery device according to Embodiment 3.
FIG. 10(d) is a structural schematic diagram of the position locking device in the sliding handle under the release-unlocked state of the stent in the delivery device according to Embodiment 3.
Figure 10:
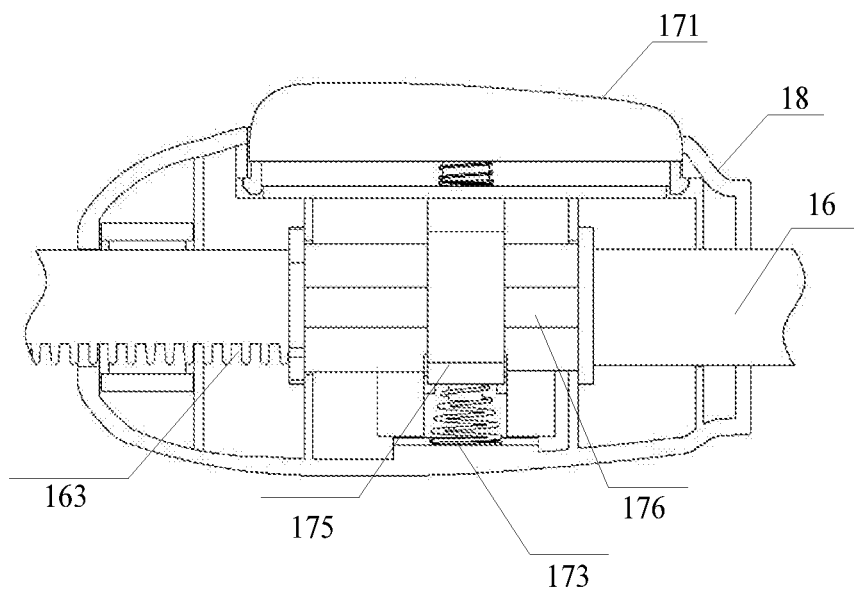
Figure 10:
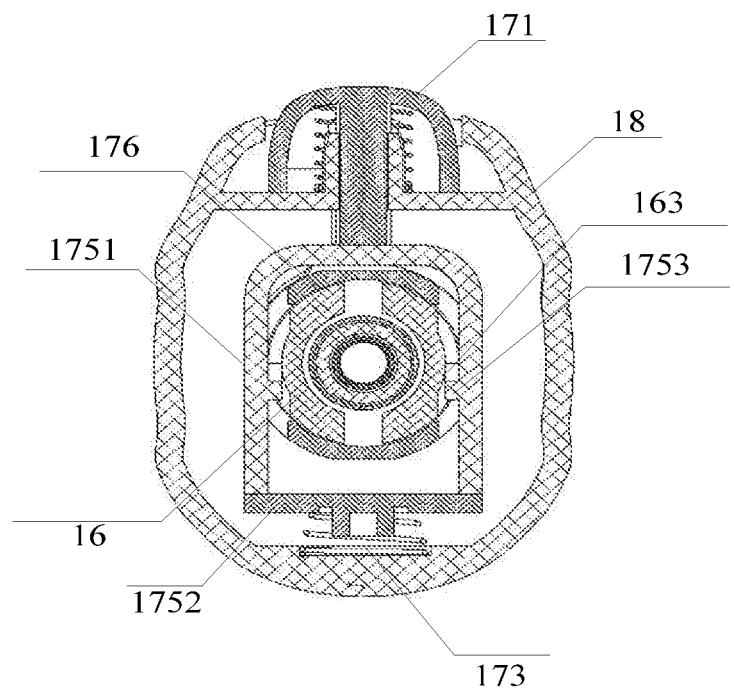
Figure 10:
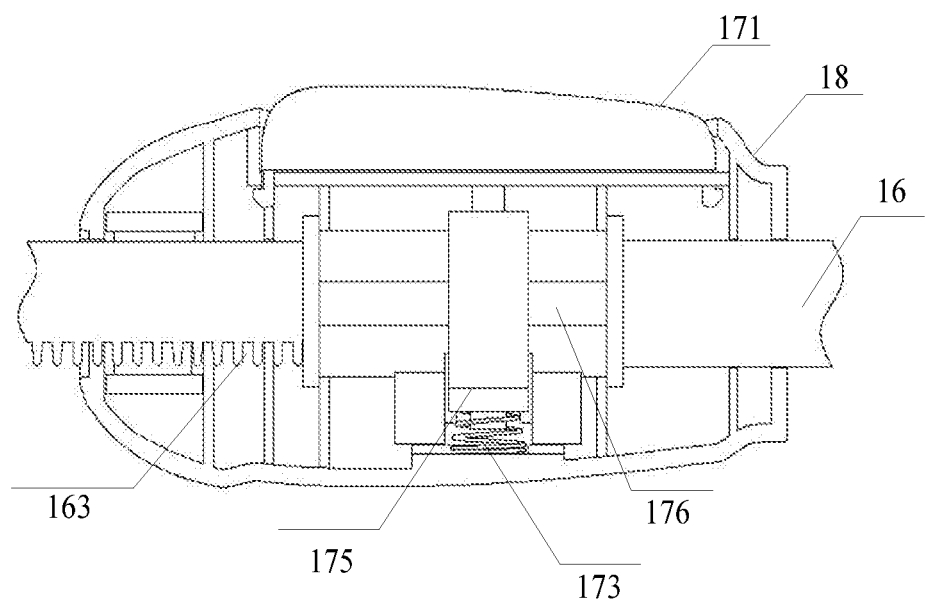
Figure 13:
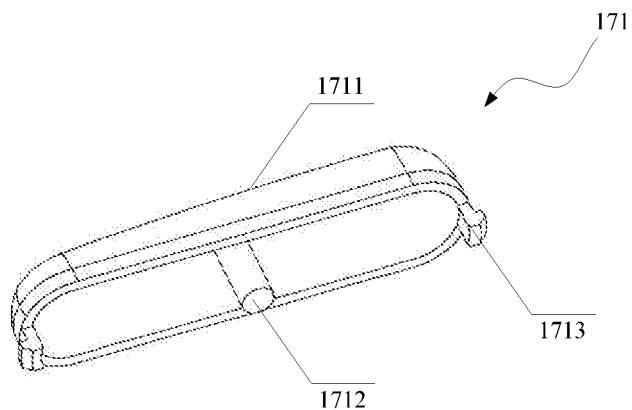
FIG. 13 is a structural schematic diagram of a key of the delivery device according to Embodiment 7.

In Embodiment 7, as shown in FIG. 13, at least one second fixing member 1713 is provided at the inner side edge of the key 1711, and when the key assembly 171 is not pressed, the second fixing member 1713 abuts against the inner side edge of the opening at the top of the sliding handle 18 (as shown in FIG. 10(*b*)) to prevent the key assembly 171 from sliding out of the opening of the sliding handle 18. When the key assembly 171 is pressed, the second fixing member 1713 is separated from the inner side edge of the opening at the top of the sliding handle 18 (as shown in FIG. 10(*d*)).

Embodiment 8

In Embodiment 8, another elastic component 177 is provided inside of the sliding handle 18 at the top; the elastic component 177 is sleeved on the periphery of the key support 1712 and is positioned between the key assembly 171 and the tooth block 172 (or the tooth block 175). Further, the elastic component 173 and the elastic component 177 are both springs.

In this embodiment, there is a gap between the key support 1712 and the tooth block 172 (or the tooth block 175), and a distance between the key support 1712 and the tooth block 172 (or the tooth block 175) is less than the pressing route of the key assembly 171. When the key assembly 171 is pressed, the elastic component 177 is compressed, where upon the length of the key support 1712 is greater than or equal to the current length of the elastic component 177, so that the key support 1712 contacts the top of the tooth block 172 (or the tooth block 175), thereby driving the tooth block 172 (or the tooth block 175) to compress the elastic component 173. When the key assembly 171 is released, the key support 1712 may be separated from the tooth block 172 (or the tooth block 175) under the support of the elastic component 177.

Figure 14:
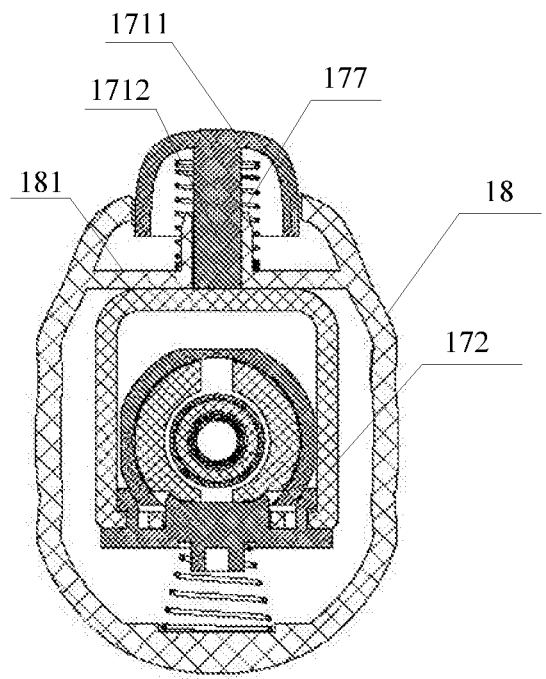
FIG. 14(a) is a front cross-sectional diagram of a sliding handle of the delivery device according to Embodiment 8 in a position-locked state.
FIG. 14(b) is a side sectional diagram of the sliding handle of the delivery device according to Embodiment 8 in an unlocked state.
Figure 14:
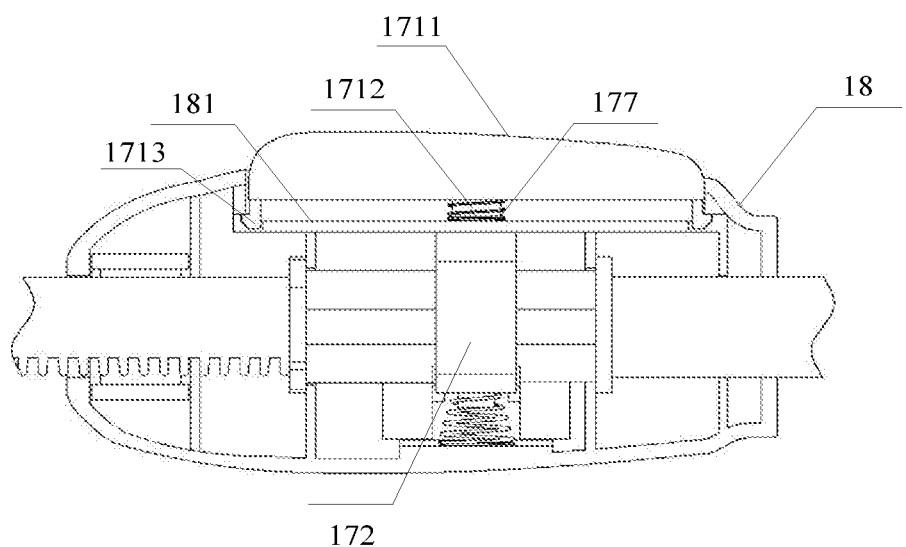

Further, referring to FIGS. 14(*a*)-14(*b*), a transverse plate 181 may be provided on the sliding handle 18, and both ends of the transverse plate 181 are separately fixed to the sliding handle 18. An opening (not shown in Figure) is provided in the middle of the transverse plate 181, and both ends of the opening are separately provided with a protrusion (not shown in Figure) in the direction of the key assembly 171. The key support 1712 may be contacted with the tooth block 172 through the opening in the middle of the transverse plate 181, and one end of the elastic component 177 is sleeved on the key support 1712 and the other end thereof is sleeved on the protrusion of the transverse plate 181. The provision of the transverse plate 181 on the sliding handle 18 allows the key to be more stable during movement without shifting, and also limits the distance that the tooth block 172 slides upwardly.

Embodiment 9

Figure 15:
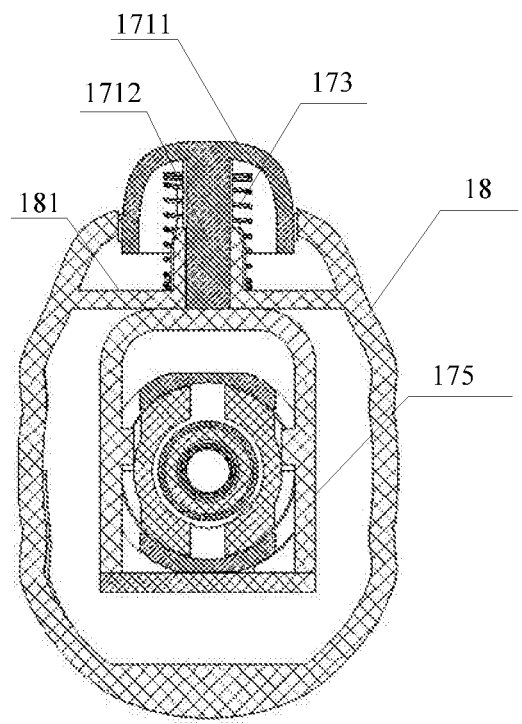
FIG. 15(a) is a front cross-sectional diagram of the sliding handle of the delivery device according to Embodiment 9 in a position-locked state.
FIG. 15(b) is a front sectional diagram of the sliding handle of the delivery device according to Embodiment 9 in an unlocked state.
Figure 15:
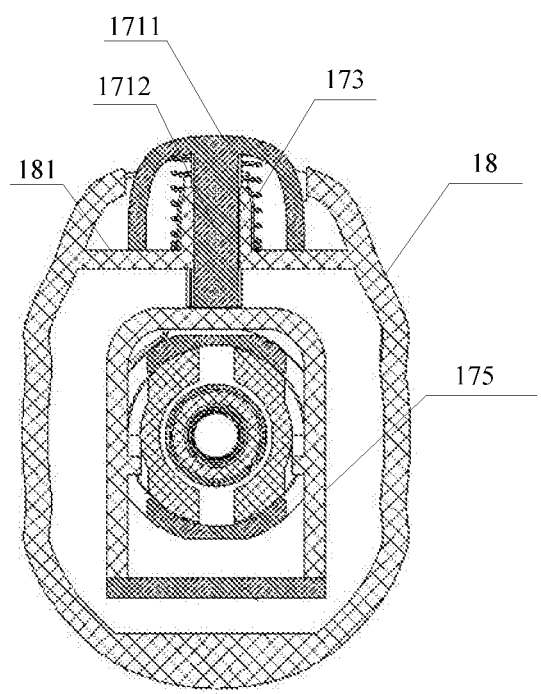

Referring to FIGS. 15(*a*)-15(*b*), in Embodiment 9, the elastic component 173 of the position locking device 17 (not shown in Figure) is provided inside of the sliding handle 18 at the top, and a transverse plate 181 is provided inside of the sliding handle 18 at the top, with an opening is provided in the transverse plate 181. One end, close to the tooth block 175, of the key support 1712 passes through the opening and is fixedly connected to the tooth block 175; the elastic component 173 is sleeved on the periphery of the key support 1712, and is positioned between the key 1711 and the transverse plate 181. Further, protrusions (not shown in Figure) are provided at both ends of the opening of the transverse plate 181 in the direction of the key 1711.

Since the key support 1712 is fixedly connected to the tooth block 175, when the key assembly 171 (not shown in Figure) is pressed, the elastic component 173 is compressed, and the key assembly 171 drives the tooth block 175 to move towards the bottom of the sliding handle 18 (namely, the tooth block 175 moves downwards). When the tooth block 175 moves downwards until the first engagement structures 163 are separated from the second engagement structure 1753, the stent is in a releasable state and the sliding handle 18 can move axially along the guide rod 16. When the key assembly 171 is released, the elastic component 173 returns and drives the key assembly 171 to move towards the top of the sliding handle 18 (namely, the tooth block 175 moves upwards), and the key assembly 171 drives the tooth block 175 to move upwards. When the tooth block 175 moves upwards until the first engagement structures 163 and the second engagement structure 1753 are engaged together, the stent is in a release-locked state, and the sliding handle 18 cannot move axially along the guide rod 16.

It can be noted that the tooth block 175 of Embodiment 9 may be replaced with the tooth block 172 of the embodiments described above, and accordingly, other components of the position locking device 17 that cooperate with the tooth block 172 will be described with reference to the embodiments described above and will not be described further herein.

The various technical features of the above-mentioned embodiments may be combined in any way, and in order to simplify the description, not all possible combinations of the technical features of the above-mentioned embodiments are described. However, as long as there is no conflict between these technical features, they should be considered to be within the scope of the description.

The embodiments described represent only a few embodiments of the present disclosure, the description of which is detailed, but should not be construed to limit the scope of the present disclosure. It can be noted that several variations and modifications may be made by those of ordinary skill in the art without departing from the spirit of the present disclosure, which all fall within the scope of the present disclosure.

The invention claimed is:

1. A delivery device for conveying an implant, comprising:
   a holder;
   a guide rod;
   a sliding handle; and
   a position locking device comprising a tooth block and a first elastic component, wherein one end of the guide rod is connected to the holder, and a second end of the guide rod penetrates through the sliding handle, an outer surface of the guide rod is provided with a plurality of first engagement structures axially spaced apart from each other along the guide rod, the position locking device is provided in the sliding handle, the tooth block is sleeved on the guide rod and provided with a second engagement structure, the first elastic component is provided inside the sliding handle, one end of the first elastic component is connected to the tooth block and a second end of the first elastic component is connected to an inner wall of the sliding handle at a bottom of the inner wall, the first elastic component and the tooth block cooperate to allow the plurality of first engagement structures and the second engagement structure to engage with each other when the first elastic component is one of not compressed or partially compressed, the sliding handle cannot move axially along the guide rod, allowing the implant to be in a release-locked state, and the implant is in a releasable state when the first elastic component is compressed until the plurality of first engagement structures and the second engagement structure are separated.

2. The delivery device according to claim 1, wherein the tooth block further comprises:
   a U-shaped support member and
   a baffle connected to an open end of the support member, the second engagement structure of the tooth block is provided on a surface of the baffle facing an inner side of the support member, and the plurality of the first engagement structures of the guide rod surrounds the outer surface of the guide rod, or the plurality of the first engagement structures of the guide rod is positioned on a part of the outer surface of the guide rod.

3. The delivery device according to claim 2, wherein the position locking device further comprises:
   a guide rod sleeve sleeved on the outer surface of the guide rod, an opening is formed in a side wall of the guide rod sleeve, both ends of the opening along the axial direction of the guide rod sleeve are respectively provided with a guide rail, two opposite sliding blocks are provided on the baffle, the tooth block is sleeved on the outer surface of the guide rod sleeve, the second engagement structure on the baffle corresponds to the opening, and the two opposite sliding blocks on the baffle respectively penetrate through the two guide rails of the guide rod sleeve.

4. The delivery device according to claim 1, wherein the tooth block further comprises:
   a U-shaped support member and
   a baffle connected to an open end of the support member, the second engagement structure of the tooth block is provided on an inner wall of the support member, and the plurality of first engagement structures of the guide rod surrounds the outer surface of the guide rod, or the plurality of first engagement structures of the guide rod is positioned on a part of the outer surface of the guide rod.

5. The delivery device according to claim 4, wherein the position locking device further comprises:
   a guide rod sleeve sleeved on the outer surface of the guide rod, two opposite guide rails are provided at a bottom of the guide rod sleeve along the axial direction, one or two openings are provided on a side wall of the guide rod sleeve, two opposite sliding blocks are provided on the baffle, the tooth block is sleeved on the outer surface of the guide rod sleeve, the second engagement structure on the support member corresponds to the opening, and the two opposite sliding blocks on the baffle respectively penetrate through the two opposite guide rails of the guide rod sleeve.

6. The delivery device according to claim 3, wherein both ends of the guide rod sleeve are respectively provided with a first fixing member for connecting to an inner wall of the sliding handle.

7. The delivery device according to claim 1, wherein the position locking device further comprises:
   a key assembly comprising a key and a key support, one end of the key support is connected to the key, the other end thereof is connected to a top of the tooth block, or the other end thereof is connected to the top of the tooth block when the key assembly is pressed, and
   when the key assembly is pressed, the first elastic component is compressed.

8. The delivery device according to claim 7, wherein a second elastic component is provided inside of the sliding handle at a top thereof, a transverse plate is provided inside of the sliding handle at the top, with an opening provided on the transverse plate, one end, close to the tooth block, of the key support penetrates through the opening and is connected to the tooth block, the second elastic component is sleeved on a periphery of the key support and is positioned between the key and the transverse plate.

9. The delivery device according to claim 7, wherein a second elastic component is further provided inside of the sliding handle at the top, the second elastic component is sleeved on a periphery of the key support, and is positioned between the key assembly and the tooth block.

10. The delivery device according to claim 7, wherein the top of the sliding handle is provided with an opening through which the key passes or fills.

11. The delivery device according to claim 7, wherein the key assembly is provided with at least one second fixing member and, when the key assembly is not pressed, the at least one second fixing member abuts against an inner side edge of an opening at the top of the sliding handle.

12. The delivery device according to claim 1, wherein the plurality of first engagement structures axially spaced apart from each other along the guide rod is provided parallel to one another and are spaced equidistantly.

13. The delivery device according to claim 12, wherein the plurality of first engagement structures is perpendicular to an axial direction of the guide rod.

14. The delivery device according to claim 1, wherein the guide rod has a chute extending in an axial direction thereof, and the plurality of first engagement structures is positioned on the outer surface of the guide rod adjacent to both sides of the chute.

* * * * *